United States Patent
Yousefian

(12) 
(10) Patent No.: US 10,010,383 B2
(45) Date of Patent: Jul. 3, 2018

(54) DUAL EXPANDING PALATAL DISTRACTOR

(71) Applicant: Joseph Yousefian, Bellevue, WA (US)

(72) Inventor: Joseph Yousefian, Bellevue, WA (US)

(*) Notice: Subject to any disclaimer, the term of this patent is extended or adjusted under 35 U.S.C. 154(b) by 0 days.

(21) Appl. No.: 15/076,441

(22) Filed: Mar. 21, 2016

(65) Prior Publication Data

US 2016/0270883 A1    Sep. 22, 2016

Related U.S. Application Data

(60) Provisional application No. 62/135,467, filed on Mar. 19, 2015.

(51) Int. Cl.
*A61C 7/10*    (2006.01)

(52) U.S. Cl.
CPC ...................... *A61C 7/10* (2013.01)

(58) Field of Classification Search
CPC ........................................................ A61C 7/10
USPC ............................................................ 433/7
See application file for complete search history.

(56) References Cited

U.S. PATENT DOCUMENTS

| | | | |
|---|---|---|---|
| 3,454,001 A | 7/1969 | Stockfisch | |
| 3,977,082 A | 8/1976 | Siatkowski | |
| 4,144,643 A * | 3/1979 | Krygier | A61C 7/10 433/7 |
| 4,348,179 A | 9/1982 | Nardella | |
| 5,439,377 A * | 8/1995 | Milanovich | A61C 7/10 433/7 |
| 5,564,920 A | 10/1996 | Klapper et al. | |
| 5,645,422 A | 7/1997 | Williams | |
| 6,109,916 A * | 8/2000 | Wilcko | A61C 7/00 433/24 |
| 6,220,856 B1 * | 4/2001 | Carano | A61C 7/10 433/7 |
| 6,299,439 B1 * | 10/2001 | Kooiman | A61C 7/10 433/7 |
| 6,358,255 B1 | 3/2002 | Testa | |
| 7,331,781 B1 * | 2/2008 | Bandeen | A61C 7/10 433/7 |
| 2003/0050641 A1 | 3/2003 | Mommaerts | |
| 2014/0186788 A1 * | 7/2014 | Sheibani Nia | A61C 7/18 433/7 |
| 2015/0231179 A1 * | 8/2015 | Sahin | A61C 7/10 433/24 |

FOREIGN PATENT DOCUMENTS

WO    2013117791 A1    8/2013

* cited by examiner

*Primary Examiner* — Nicholas Lucchesi
(74) *Attorney, Agent, or Firm* — Timothy E. Siegel Patent Law, PLLC; Timothy E. Siegel

(57) ABSTRACT

An orthodontic distractor includes two rods connected to rotatable head members. The two rods are couplable to one or more of upper teeth or palatal bones of a patient. The rotatable head members have threaded holes and pairs of the rotatable head members have opposite hand threads. The screw system also includes two twin screws that have threaded ends of opposite hand threads. Each of the two twin screws is engaged to threads of a pair of the rotatable head members. Rotation of one of the twin screws causes the pair of rotatable head members and the ends of the rods to either move together or move apart. The two twin screws are independently rotatable to cause independent expansion or contraction of different portions of the screw system.

12 Claims, 13 Drawing Sheets

DUAL EXPANDING PALATAL DISTRACTOR

CROSS-REFERENCE TO RELATED APPLICATION

This application claims the benefit of U.S. Provisional Patent Application No. 62/135,467, filed Mar. 19, 2015, which is incorporated herein by reference in its entirety.

BACKGROUND

Orthodontists and dental researchers are constantly searching for new and improved ways to correct the problem of upper jaw constriction with collapsed dental arch causing lingual cross bites or overly wide upper jaw and dental arch causing buccal posterior cross bites.

Posterior cross bites are the most common dental malocclusion in young or adult patients due to various etiologies. The condition due to insufficient maxillary arch width in various dimensions can cause further skeletal growth problems if left untreated. The overgrown width of the upper jaw also by causing buccal cross bite can cause significant damage to the dentition and growth of the temporomandibular joints. Expansion of the maxilla relies on rapid palatal expander devices that deliver forces to break the mid-palatal and circum-maxillary sutures to facilitate transverse and sagital dento-facial correction.

Current orthodontic devices for spreading the jaws, dental arches, or contracting the dental arches have not been entirely satisfactory because such devices are capable of performing only one of parallel expansion, parallel contraction, fan shape expansion, or fan shape contraction of the jaws and dental arches. Current expansion appliances such as HYRAX (tooth borne) and HAAS expander (tooth and tissue borne) designs are limited to transverse bilateral and parallel expansion in the posterior region of the maxilla. As a result, they lack the differential nonparallel expansion or contraction capability unless sequentially used in combination with fan shape design expanders. As a result, in most cases with V-shape maxillary arch forms (wider in the back than front), during the expansion of the premolar or canine sections to proper width, the molar areas can get over-expanded, causing buccal cross bite in the molar areas. This impact can be opposite in significant U-shape maxillary constriction, causing the premolar and canine teeth end up in over-extend or buccal cross bite as the molar areas are expanded to the ideal width.

SUMMARY

Embodiments of expander devices described herein provide improved orthodontic appliances and protocol for expanding or contracting the jaws and dental arches as well as enlarging the nasal cavity and upper pharyngeal airway.

This palatal expander design gives the clinician the ability to direct expansion or constriction forces to various segments of the maxillary arch in nonparallel configuration.

In some embodiments described herein, expander devices provide an arch spreading or contracting device and protocol that is simple in structure and use, that avoids the defects and insufficiencies of the presently available devices, and that, at the same time, are capable of differential nonparallel expansion or contraction of the jaws and dental arches.

In some embodiments described herein, expander devices provide a jaw and dental arch spreading capability that not only addresses the dentition and the jaw bones, but also reshapes and expands the nasal cavity and palatal soft tissue, as well as enlarging the nasal airway and behind the soft palate airway (retropalatal). This can be accomplished by enlarging the mouth and accommodating the position of the tongue forward out of the pharynx, and by enlarging the airway behind the tongue (retroglossal) and below and behind the tongue (hypoglossal). This will contribute in enlarging the nasopharyngeal airway by expanding the environment of the upper airway starting from nostrils, nasal cavity retropalatal area, retroglossal area, and hypoglossal area.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
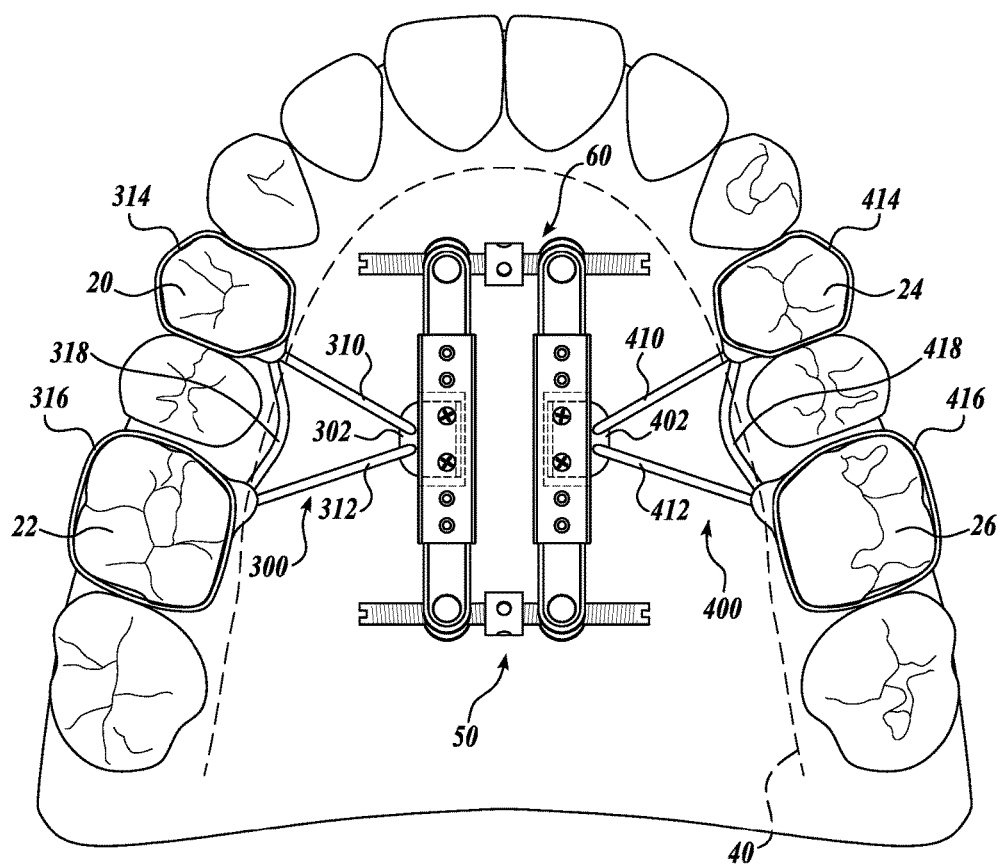
FIG. 1 shows a bottom view of a palatal distractor according to a first representative embodiment of the present disclosure, wherein the palatal distractor is installed on the upper palate of a patient.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Likewise, unless otherwise noted, any steps described herein are not limited to a particular order, such that steps may be rearranged in some instances to achieve the same or substantially similar result.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "forward," "rearward," "upper," "lower," "left," "right," etc. These references, and other similar directional references in the present application, are only to assist in helping describe and to understand the particular embodiment and are not intended to limit the present disclosure to these directions or locations.

The following discussion provides examples of methods and orthodontic apparatuses that include a screw device for stretching or contracting a patient's dental arches sideward or inward horizontally, expanding the upper jaw bone, as well as enlarging the palate, oral cavity, nasal cavity and upper nasopharyngeal airway. This expander design gives the clinician the ability to direct expansion or constriction forces to various segments of the dental arches, and expansion of maxillary jaw as well as nasal cavity in nonparallel configuration.

One purpose of the apparatuses described herein is to provide an expansion and constriction screw apparatus which can be used in multipurpose manner to not only expand the front and back teeth and sections of the upper jaw and nasal cavity in nonparallel ways in transverse directions, respectively, but also to effectively constrict the maxillary dental arch front and back teeth.

This purpose is achieved, in some embodiments, by connecting respective ends of rods rotatable head members with a threaded hole where the threads of the threaded holes are of opposite hand on each side, and by providing a twin screw on respective ends of the rods which is in threaded engagement with the threaded holes of the rotatable head members attached to the each ends of the rods. The twin screw assembly of this design makes it possible to exert independent, nonparallel, transverse expansion and constriction forces on the front and/or back teeth.

In some embodiments, the adjustable twin screw assemblies are embedded in mirror image extension plates, the separate parts of which are formed to fit against teeth and supporting soft palate on opposite sides of the upper jaw, with the plates being separated sufficiently to enable the twin screw assemblies to fit between them and to thereby adjust the relative positions of the two plate parts.

Figure 2:
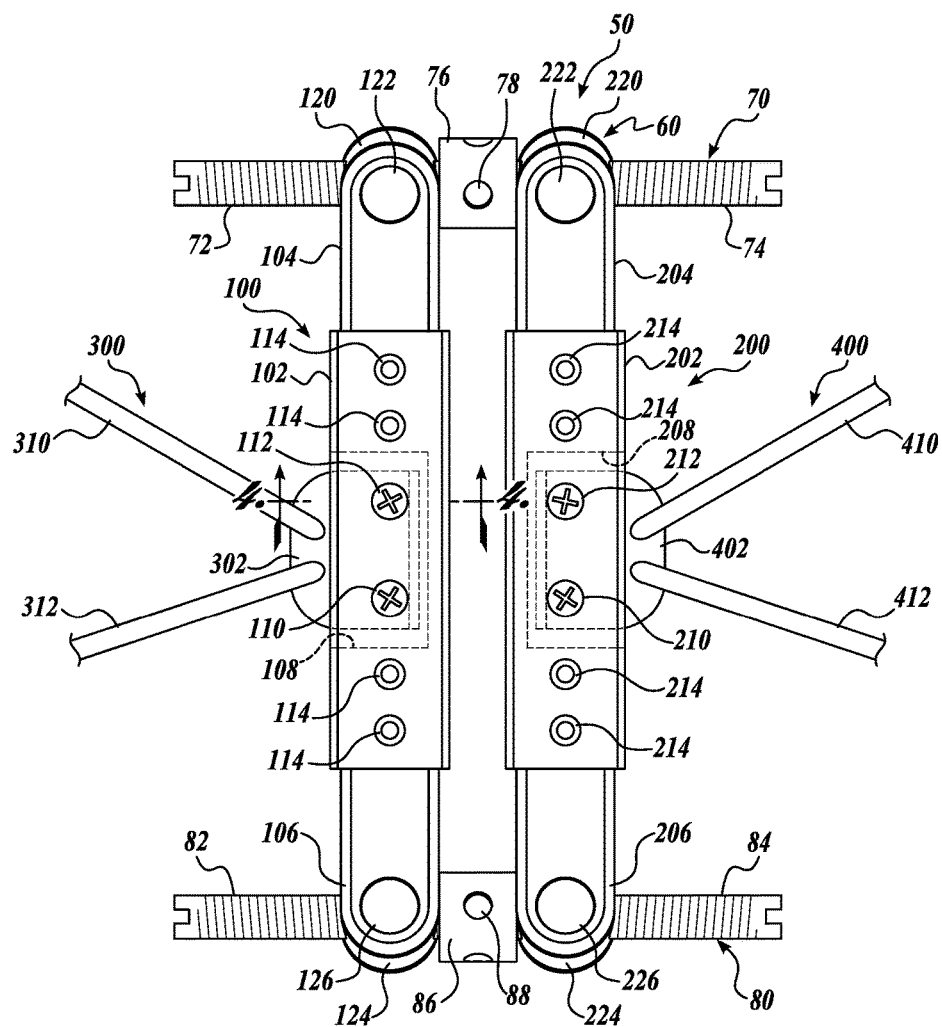
FIG. 2 shows a partial bottom view of the distractor of FIG. 1.
Figure 3:
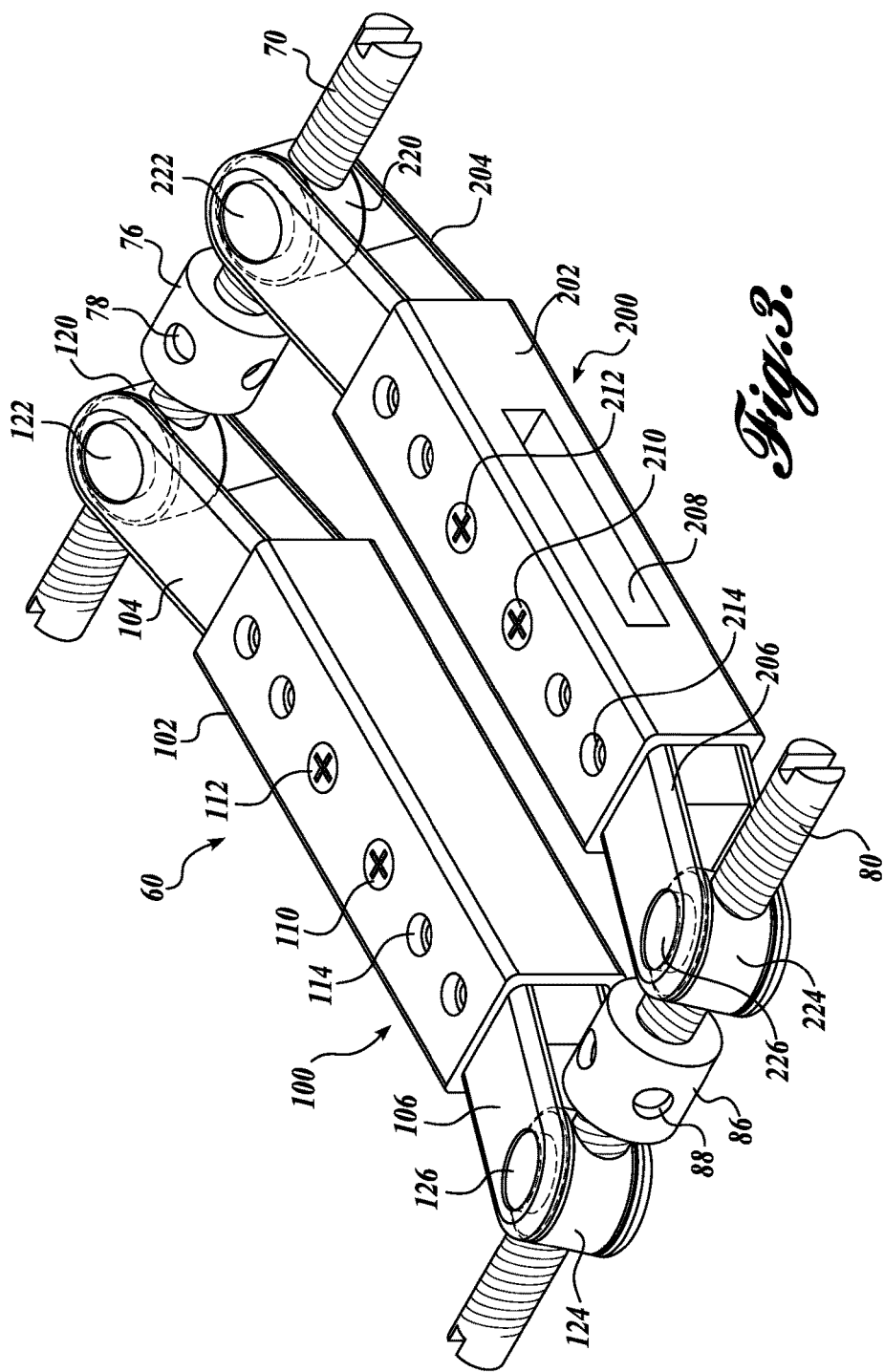
FIG. 3 show an isometric view of a screw assembly of the distractor of FIG. 1.

Referring to FIGS. 1-5, a first embodiment of a palatal distractor 50 will now be described. The distractor includes a screw assembly 60 that is coupled to one or more upper teeth and/or palatal bones of a patient by a pair of coupling assemblies 300, 400. As best shown in FIGS. 2 and 3, the screw assembly includes a first rod 100 and a second rod 200 coupled to each other by a first screw 70 and a second screw 80. In the illustrated embodiment the second rod 200 is a mirror image of the first rod 100. For the sake of brevity, the first rod 100 will be described herein with the understanding that the second rod 200 is similar to the first rod, and a component of the second rod with a reference number 2XX corresponds to a similar component 1XX of the first rod.

The first rod 100 includes a central body section 100 with a first clevis 104 disposed at a first end, and a second clevis 106 disposed at a second end. The first and second devises 104 and 106 are illustrated as being integrally formed with the central body section 100; however, embodiments are contemplated in which the clevises are formed separate from the central body section and then attached by known fasteners, adhesives, or other means. Further embodiments are contemplated in which the distance between the devises 104 and 106 is adjustable. In this regard, one or both devises 104 and 106 can be configured to slidingly engage the central body section 100 and then selectively positioned and secured in place. This and other embodiments that enable adjustment of the clevis positions are contemplated and should be considered within the scope of the present disclosure.

A first rotatable head member 120 is positioned between the arms of the first clevis 104. Trunnions 122 extend from opposing sides of the first rotatable head member 120, and each trunnion is received within a hole formed in one of the arms of the first clevis 104. In this manner, the first rotatable head member 120 is rotatably mounted to the first clevis 104 about an axis that passes through the center of the trunnions 122. At the other end of the rod 100, a second rotatable head member 124 has trunnions 126 extending from opposite sides to rotatably mount the second rotatable head member to the second clevis 106 in a manner similar to the mounting of the first rotatable head member 120 to the first clevis 104. Each of the rotatable head members 120 and 124 is respectively provided with threaded to threadedly engage the first end 72 and 82 of first and second twin screws 70 and 80, respectively.

The first twin screw 70 has a first end 72 with threads formed thereon. The first end 72 of the first twin screw 70 threadedly engages the threaded hole formed in the first rotatable head member 120 of the first rod 100. A second end 74 of the first twin screw 70 also has threads formed thereon, wherein the threads of the first end 72 are of the opposite hand of the threads of the second end. The second end 74 first twin screw 70 is threadedly engaged with the threaded hole formed in first rotatable head member 220 of the second rod 200. Thus, rotation of the first twin screw 70 in a first direction moves the first rotatable head members 120 and 220, and therefore, the first ends of the first and second rods 100 and 200, away from each other. Conversely, rotation of the first twin screw 70 in a second direction moves the first a rotatable head members 120 and 220, and therefore, the first ends of the first and second rods 100 and 200, towards each other.

The middle portion of the first twin screw 70 includes a fitting 76 provided with two through-and-through openings 78 positioned perpendicular to each other 8a and 8b. The first twin screw 70 can be rotated by means of a tool inserted into one of the crossed openings 70. Other possible embodiments of the fitting 76 include flats formed on the fitting to allow a wrench to engage the flats to facilitate rotation of the first twin screw 70. These and other features that enable rotation of the first twin screw 70 are contemplated and should be considered within the scope of the present disclosure.

The second twin screw 80 is similar to the first twin screw 70, having first and second ends 82 and 84 that are threaded so that the threads of one end are of the opposite hand of the threads of the other end. The threaded ends 82 and 84 threadedly engage the second rotatable head members 124 and 224, respectively, so that rotation of the second twin screw 80 in a first direction moves the second rotatable head members 124 and 224, and therefore, the second ends of the first and second rods 100 and 200, away from each other. Conversely, rotation of the second twin screw 80 in a second direction moves the second rotatable head members 124 and 224, and therefore, the second ends of the first and second rods 100 and 200, towards each other.

Figure 4:
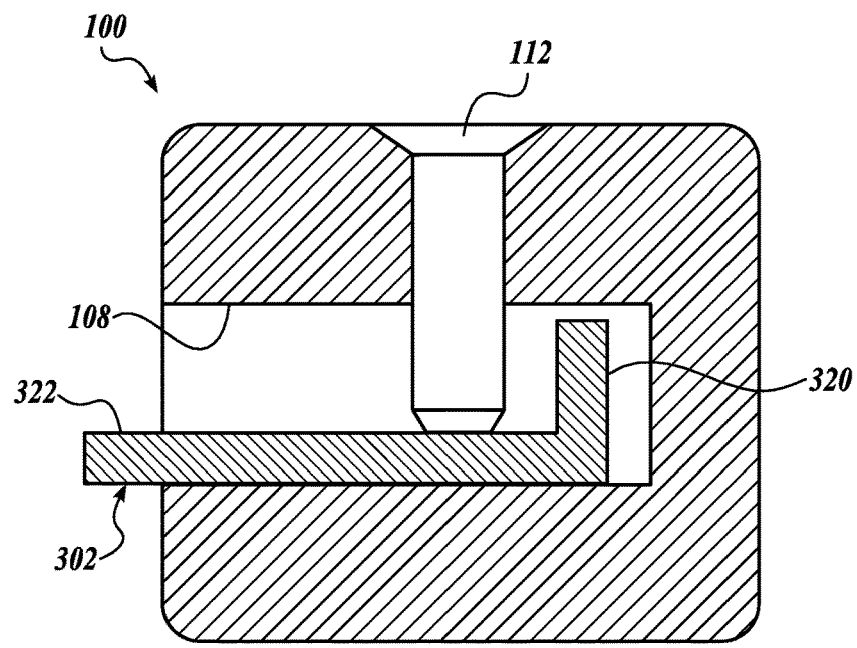
FIG. 4 shows a partial cross-sectional view of the screw assembly of FIG. 3.

Referring now to FIGS. 1, 2 and 4, a first coupling assembly 300 couples the first rod 100 to the upper right bicuspid 20 and molar 22. The first coupling assembly 300 includes a base 302 that has an L-shaped cross section. The base 302 is sized to fit within the slot 108 formed in the body 102 of the first rod 100. Set screws 110 and 112 extend from an outside surface of the body 102 into the cavity 108. As best shown in FIG. 4, the set screws engage a flat portion 322 of the base 302 to press the base against one side of the slot 108, thereby maintaining the position of the base, and therefore, the coupling assembly 300, relative to the first rod 100. A leg 230 of the base extends away from the flat portion 322 and is positioned so that the leg will engage the set screws 110 and 112 to prevent the base from disengaging with the first rod 100 unless the set screws are first loosened or removed.

Referring back to FIG. 1, the coupling assembly 300 includes extension arms 310 and 312 extending outward from the base 302 and connected by a cross-member 318. A bicuspid band 314 is coupled to one of the extension arms 310 and is sized and configured to be fitted on a bicuspid 20. A molar band 316 is couple do the other extension arm 312 and is sized and configured to be fitted on a molar 22. With the bicuspid band 315 and the molar band 316 secured to the bicuspid 20 and molar 22, respectively, the first rod is fixedly secured to one side of the mouth of the patient.

In the illustrated embodiment, the second coupling assembly 400 is a mirror image of the first coupling assembly, wherein a component of the second coupling assembly having a reference number of 4XX corresponds to a component from the first coupling assembly 300 having a reference number of 3XX. It will be appreciated that the disclosed coupling assemblies are exemplary only and should not be considered limiting.

In this regard, various other embodiments are contemplated, wherein different configurations are provided to couple the screw assembly 60 to the patients teeth, palatal bones, or a combination thereof. Moreover, various configurations are contemplated in which one coupling assembly is not a mirror image of the other coupling assembly, for example, if a patient is missing one or more teeth or has other oral asymmetries.

The use of the slotted configuration to couple base 302 to the first rod 100 allows for adjustment of the coupling assemblies 300 and 400 relative to the screw assembly 60. That is, the coupling members 300 and 400 can be located relative to the teeth/palatal bones, and then the set screws can be tightened to lock the position of the coupling assemblies to the screw assembly 60. The adjustability of the coupling members 300 and 400 in combination with the nonparallel expansion capability makes the screw assembly 60 provides a distractor that is easily adjustable to the patient. The appliance does not need to be pre-adjusted, but can be adjusted by a clinician right after the opening the packaging. Also, such a device does not require prefabrication.

Figure 5:
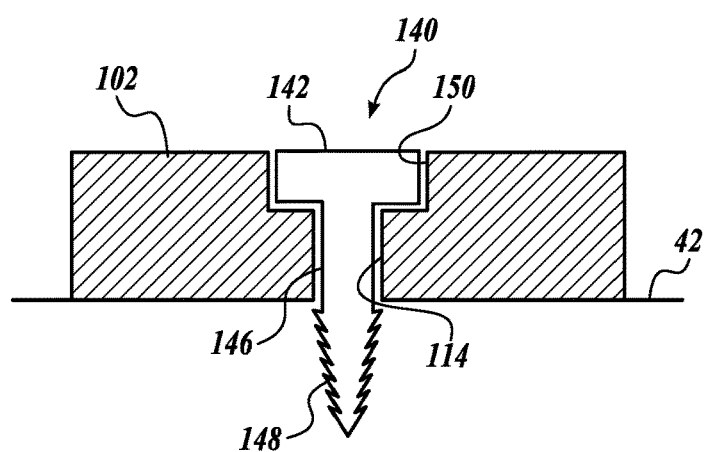
FIG. 5 shows a second partial cross-sectional view of the screw assembly of FIG. 3.

Referring to FIGS. 3 and 5, the first rod 100 further includes a plurality of apertures 114 extending therethough to allow the first rod to be secured directly to the palate of the patient using screws or other suitable fasteners. As best shown in FIG. 5, each aperture 114 has a counterbore 150 formed at the upper end. A screw 140 has a head 142, a shaft 146, and a threaded portion 148. The head 142 of the screw 140 is larger than the diameter of the aperture 114 and is received within the counterbore 150. The threaded portion 148 of the screw 140 is larger than the diameter of the aperture 114. As a result, when the screw 140 is inserted in the aperture, the body 102 of the first rod 100 is retained between the head 142 and the threaded portion 148. It will be appreciated that the screws 140 can be used in addition to or in lieu of the coupling member 300.

When the screw assembly 60 is directly coupled to a patient's palate using screws 140, the position of the screw assembly is determined by the depth of the screws.

This prevents the application of undue pressure to the palate by the screw assembly when the screws are tightened. Further, the inclusion of multiple holes on each end of each rod 102 and 104 allows a screw assembly to be secured to the palate while leaving at least one aperture 114 on each end of each rod unused. When the screw assembly 60 is removed and reinstalled, alternate holes can be used. This allows the previous insertion location of the screw to heal while an alternate screw location is used to secure the screw assembly to the palate. In some embodiments, the screws mentioned above will be used as main attachment of the expander to the roof of the patient's mouth with no other means for attachment to the teeth in cases that the patient is partially or fully edentulous with no teeth or teeth that cannot support the force of applied forces from expansion or distraction.

Figure 13:
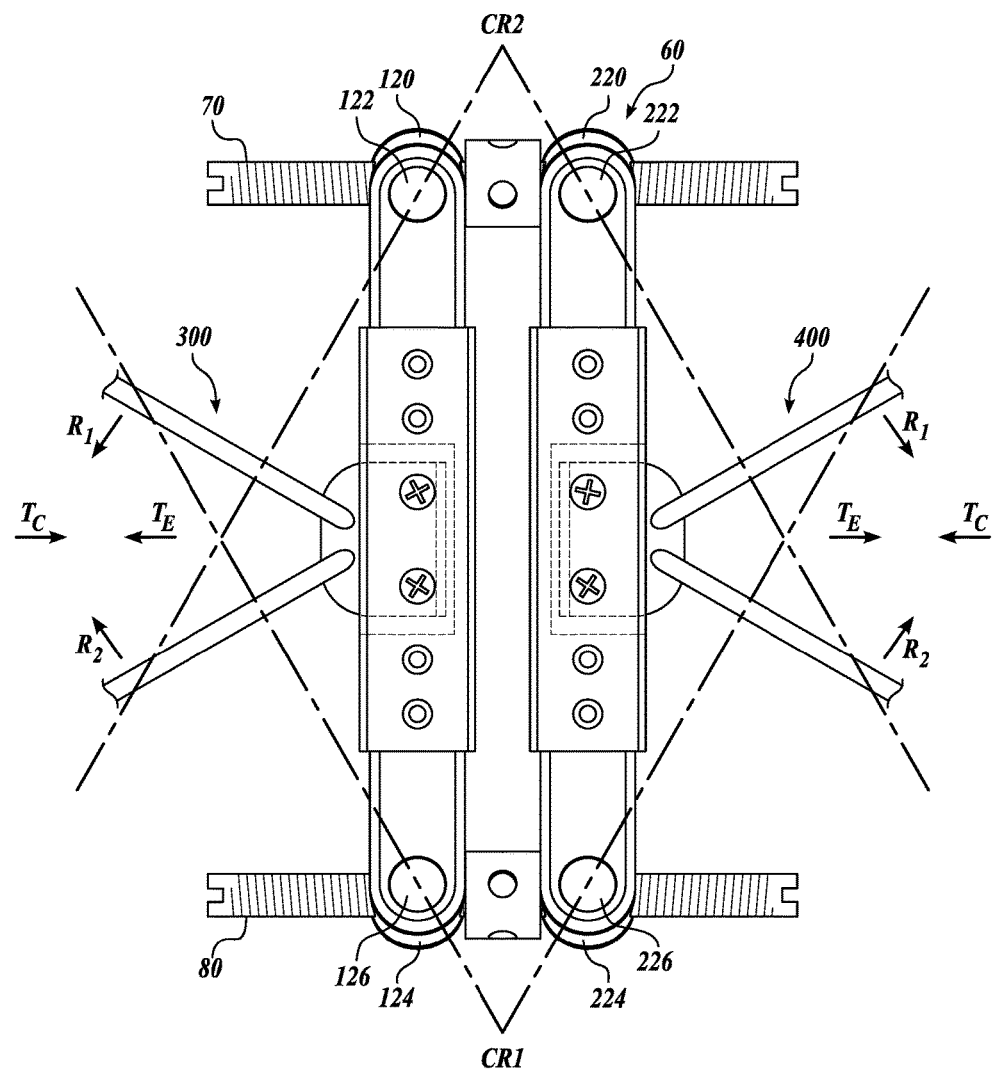
FIG. 13 shows a bottom view of the screw assembly of FIG. 3 with the directions of forces which may be exerted on the teeth and different areas of the upper jaw and airway by the distractor and around the centers of rotation.

An advantage of embodiments of the dual expander design type screw and orthodontic appliance assembly is that it is possible to select any desired variation of transverse extension and/or constriction at the front and back teeth using one appliance. FIG. 13 shows the directions of forces which may be exerted on the teeth and different areas of the upper jaw and airway and around the centers of rotation CR1, CR2 of the screw assembly 60. Transverse expansion force (TE) and transverse contraction force (TC) are achieved by rotating the first and second twin screws 70 and 80 by equal amounts, thereby maintaining the angular position of the first and second rods 100 and 200 relative to each other. Rotational forces R1 and R2 are achieved turning the first twin screw 70 and the second twin screw 80 asymmetrically so that the angular position of the first and second rods 100 and 200 changes relative to each other.

Figure 6:
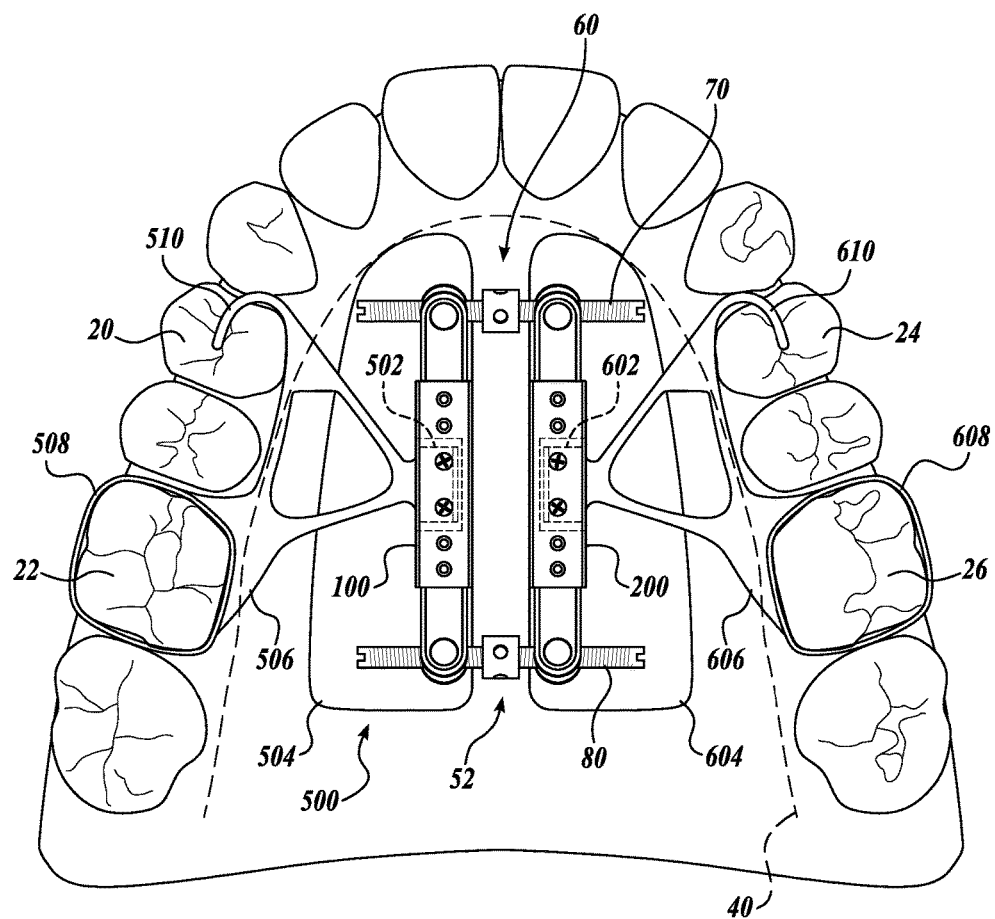
FIG. 6 shows a bottom view of a palatal distractor according to a second representative embodiment of the present disclosure, wherein the palatal distractor is installed on the upper palate of a patient.

FIG. 6 shows a first alternate embodiment of a palatal distractor 52 according to the present disclosure. The distractor includes screw assembly 60 as previously described. Coupling assemblies 500 and 600 attached the screw assembly 60 to the mouth of the patient. In the illustrated embodiment, the second coupling assembly 600 is a mirror image of the first coupling assembly 500, wherein a component of the second coupling assembly having a reference number of 6XX corresponds to a component from the first coupling assembly 500 having a reference number of 5XX. The first coupling assembly 500 will be described herein with the understanding that unless otherwise noted, the second coupling assembly 600 is a mirror image of the first coupling assembly.

The coupling assemblies 500 and 600 include left and right halves 504 and 604, respectively, of two-part acrylic palate plate custom fitted to the patient's palate. The left half 504 and a right half 604 of the palate plate are symmetrical in the disclosed embodiment; however, alternate embodiments are contemplated wherein the halves are asymmetrical.

Parts of the first ends of the first and second twin screws 70 and 80 are embedded in the right acrylic palatal plate 604. Parts of the first ends of the first and second twin screws 70 and 80 are embedded in the left acrylic palatal plate 504. Thus, the screw assembly 60 maintains the position of the left and right palatal plates 504 and 604 relative to each other. When in place, the plates 504 and 604 extend from the anterior portion of the palate behind the incisors, approximately in line with the mesial side of the first bicuspids to the posterior portion of the palate approximately in line with the mesial side of the second molars.

The first coupling assembly 500 includes a mounting fitting 506 coupled to the screw assembly 60 in a manner similar to the previously described embodiment.

Alternate embodiments are contemplated in which the mounting fitting 506 is coupled to the left palatal plate 504 or a combination of the screw assembly 60 and the left palatal plate. The illustrated embodiment further includes a molar band 508 for securing the mounting fitting 506 to a molar 22. The first coupling assembly also includes an occlusal rest arm 510 securable to the bicuspid 20 by adhesive cement or other suitable means.

Alternate embodiments are contemplated in which various combinations of bands and rest arms are utilized. For example, molar bands and bicuspid bands can be utilized. In addition, occlusal rest arms and lingual rest arms can be secured to various teeth using adhesive cement or other suitable means. These and other configurations for securing appliances to teeth, both alone or in combination with each other, are contemplated and should be considered within the scope of the present disclosure.

In some embodiments, the appliance includes plates or rods which are premade or custom fitted to the occlusal or lingual surface of the right or left first and second bicuspids and extend to the occlusal or lingual surface of right and left first or second molars. Each left and right plates or rods are securable to the patient's occlusal or lingual surface of the left and right upper first or second bicuspids and first or second molars by adhesive cement.

Figure 7:
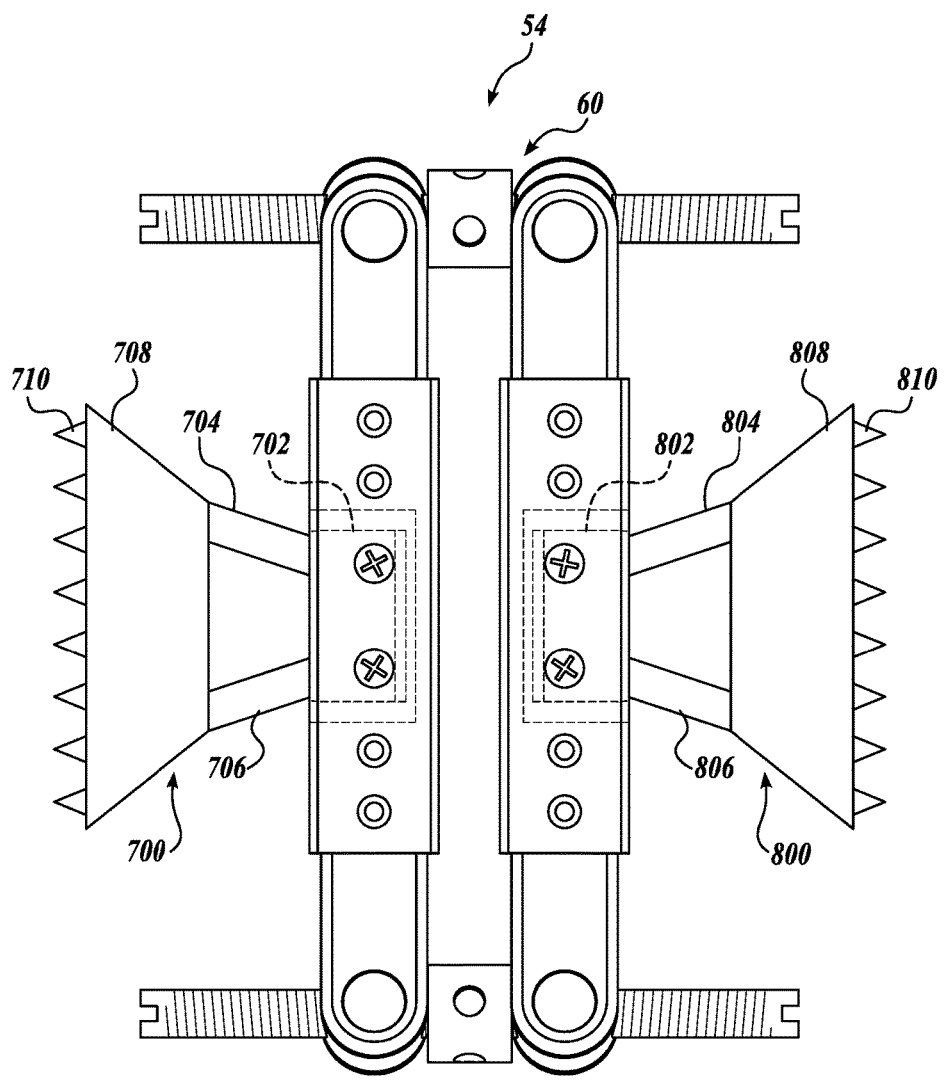
FIG. 7 shows a bottom view of a palatal distractor according to a third representative embodiment of the present disclosure.
Figure 8:
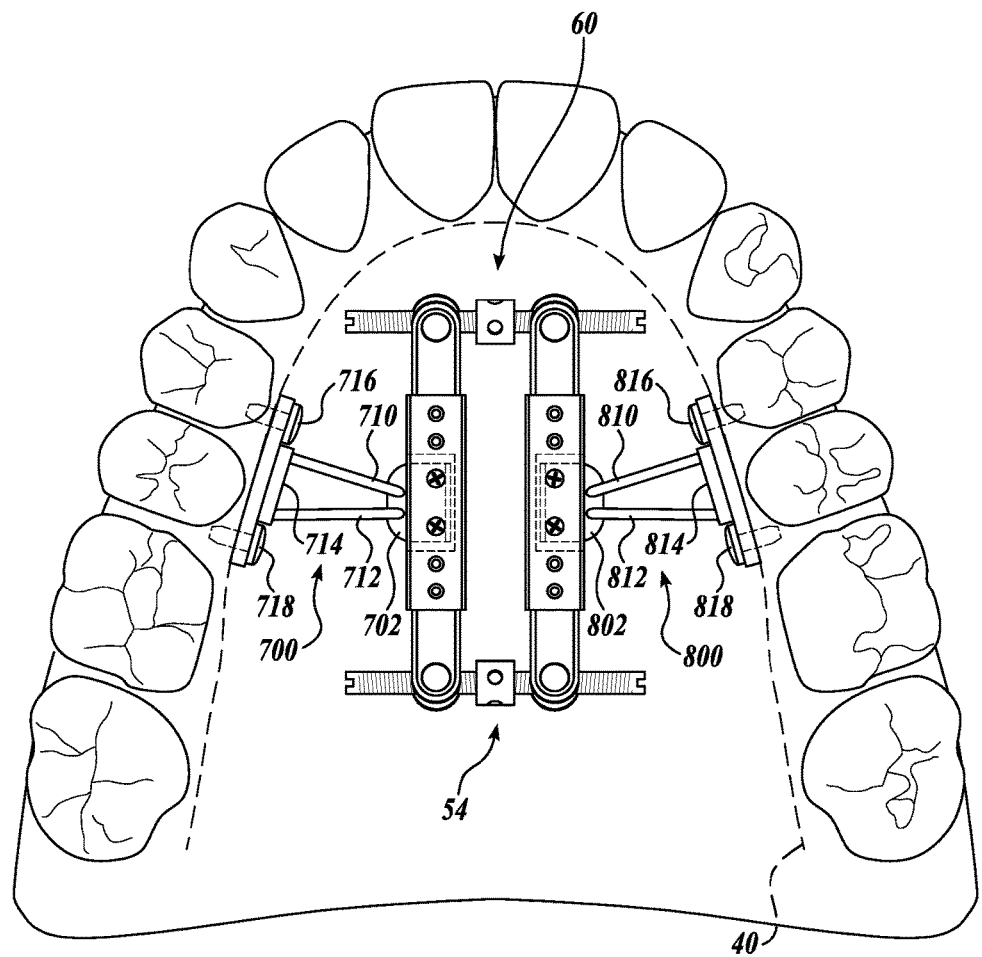
FIG. 8 shows a bottom view of the palatal distractor of FIG. 7, wherein the palatal distractor is installed on the upper palate of a patient.

FIGS. 7 and 8 show a second alternate embodiment of a palatal distractor 54 according to the present disclosure. The distractor includes screw assembly 60 as previously described. Coupling assemblies 700 and 800 attached the screw assembly 60 to the mouth of the patient. In the illustrated embodiment, the second coupling assembly 800 is a mirror image of the first coupling assembly 700, wherein a component of the second coupling assembly having a reference number of 8XX corresponds to a component from the first coupling assembly 700 having a reference number of 7XX. The first coupling assembly 700 will be described herein with the understanding that unless otherwise noted, the second coupling assembly 800 is a mirror image of the first coupling assembly.

As shown in FIG. 7, the first coupling assembly 700 is similar to previously described first coupling assembly 300, having a base 702, and first and second extension arms 704 and 706 extending therefrom. A bone-borne plate 708 is coupled to the extension arms 704 and 706 and has a plurality of insertion studs 710 disposed on the outer surface of the bone-borne plate for securing and attaching the plate in a patient's palatal bones bilaterally. FIG. 8 shows a variation of the embodiment of FIG. 7 in which the fasteners 716 and 718 are used in addition to or in lieu of the insertion studs 710 to secure the plate 714 to the patient's bones.

This bone-borne option can eliminate the need of orthodontic bands on molars and premolars and is an effective system for children at early mixed dentition with primary teeth or missing teeth in transitional stage of dental development who have upper jaw and arch constriction, excessive upper arch expansion, cross bite (unilateral/bilateral), and/or severe upper airway constriction. This bone-borne embodiment may need surgical intervention for insertion of the appliance into the patient's mouth under sedation and local anesthesia.

Figure 9:
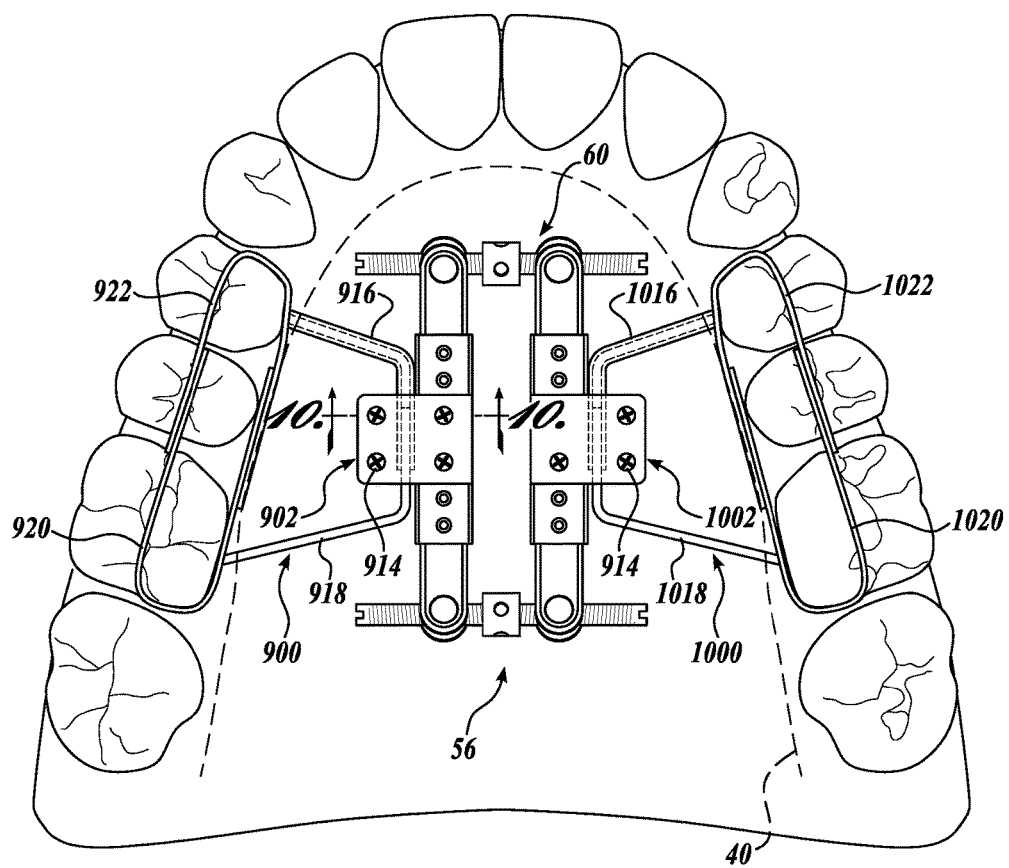
FIG. 9 shows a bottom view of a palatal distractor according to a fourth representative embodiment of the present disclosure, wherein the palatal distractor is installed on the upper palate of a patient.
Figure 10:
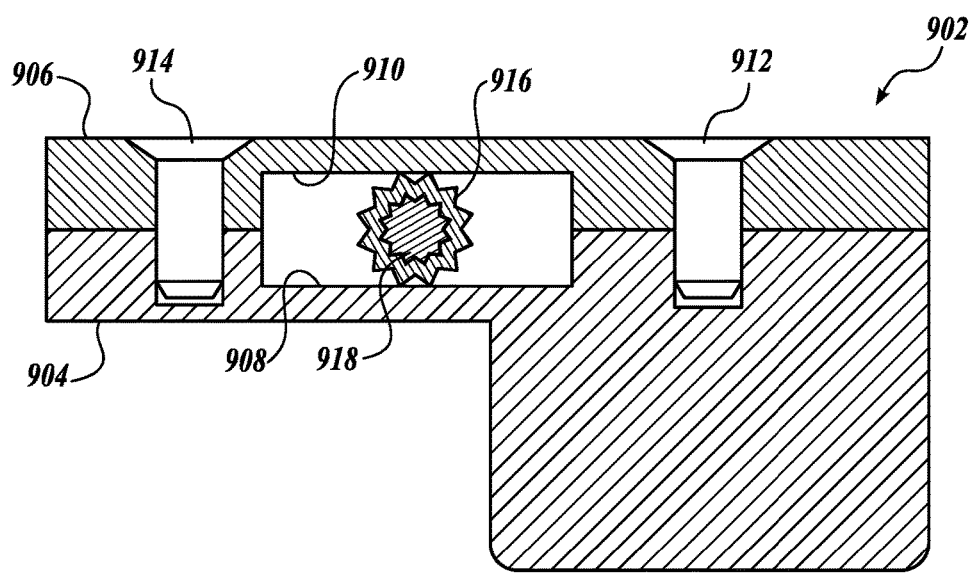
FIG. 10 shows a partial cross-sectional view of the distractor of FIG. 9.

FIGS. 9 and 10 show a third alternate embodiment of a palatal distractor 56. The distractor 56 includes screw assembly 60 as previously described. Coupling assemblies 900 and 1000 attached the screw assembly 60 to the mouth of the patient. In the illustrated embodiment, the second coupling assembly 1000 is a mirror image of the first coupling assembly 900, wherein a component of the second coupling assembly having a reference number of 10XX corresponds to a component from the first coupling assembly 900 having a reference number of 9XX. The first coupling assembly 900 will be described herein with the understanding that unless otherwise noted, the second coupling assembly 000 is a mirror image of the first coupling assembly.

As best shown in FIG. 9, the first coupling assembly 900 includes a first arm 916 coupled to a U-shaped forward band portion 922. A first end 926 of the forward band portion 922 is secured to an occlusal portion of one or more teeth using adhesive cement or other suitable means. A second end 928 of the forward band portion 922 is secured to a lingual portion of one or more teeth using adhesive cement or other suitable means. The first coupling assembly also includes a second arm 918 coupled to a U-shaped rear band portion 920. Similar to the forward band portion 922, the rear band portion 920 includes a first end 930 and a second end 932 secured to the lingual and occlusal portions, respectively, of one or more teeth by adhesive cement or other suitable means.

Referring now to FIG. 10, the end of the first arm 916 is hollow, with an inner aperture sized and configured to slidably receive the second arm 918. In the illustrated embodiment, the aperture has a starburst cross-section that corresponds to the outer surface of the second arm 918. In this manner, the rotational position of the first arm 916 relative to the second arm 918 can be selectively controlled. It will be appreciated that the shape of the aperture of the first arm 916 and the corresponding outer surface of the second arm 918 can be triangular, square, or any other shape that will resist rotation between the arms. Further the shape of the outer surface of the first arm 916 can also be triangular, square, or any other shape that will resist rotation between the first arm and the base 902 of the coupling assembly 900.

The arms 916 and 918 are secured to the screw assembly 60 between lower clamping element 904 and upper clamping element 906. Fasteners 912 and 914 secure the clamping elements together to retain the second arm within the first arm and to secure the coupling assembly 900 to the screw assembly. The disclosed clamping configuration allows for the position of the arms 916 and 918 relative to the screw assembly 60 to be selectively adjustable. This adjustability, combined with the adjustability of the arms 916 and 918 relative to each other, allows for the position of the forward and rear band portions 922 and 920 to be easily adjusted to fit the mouth of the patient.

Figure 11:
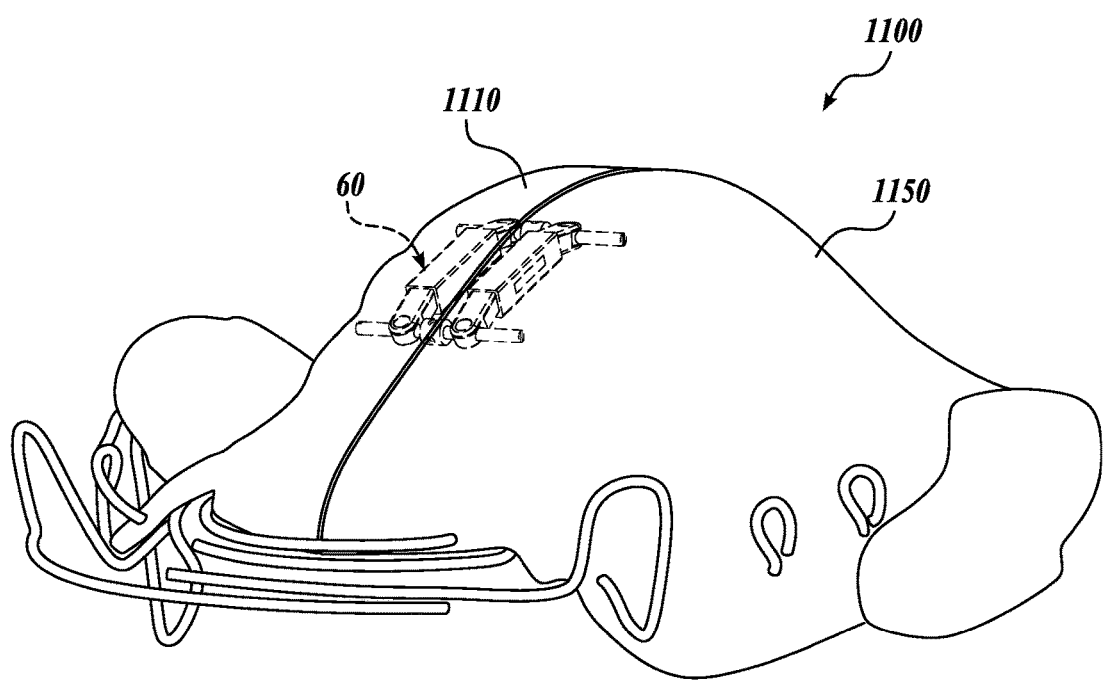
FIG. 11 shows an isometric view of a maxillary jaw dental arch according to a fifth representative embodiment of the present disclosure.
Figure 12:
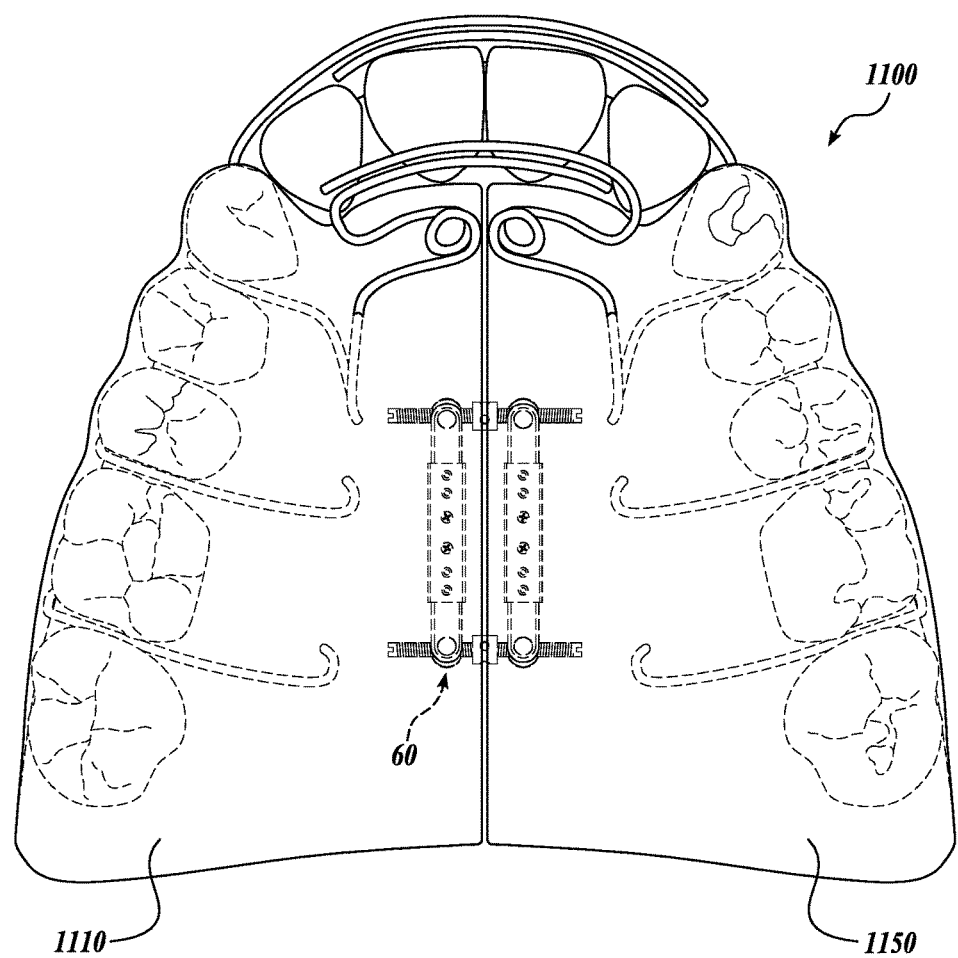
FIG. 12 shows a bottom view of the maxillary jaw dental arch of FIG. 11.

Referring to FIGS. 11 and 12, a fourth alternate embodiment in the form of a removable palatal distractor 1100 is shown. The distractor 1100 includes a first palatal plate 1100 coupled to a second palatal plate 1150 by the previously described screw assembly. In the illustrated embodiment, the second palatal plate 1150 is a mirror image of the first palatal plate 1100, wherein a component of the second palatal plate having a reference number of 115X corresponds to a component from the first palatal plate 1100 having a reference number of 111X. The first palatal plate 1100 will be described herein with the understanding that unless otherwise noted, the second palatal plate 1150 is a mirror image of the first palatal plate.

The first palatal plate 1100 is formed of acrylic or other suitable material and is preferably formed from a mold of the patient's maxillary dental arch. A plurality of posts 1114 and 1116 are molded into the palatal plate 1100 and extend therefrom to engage the patient's teeth when distractor 1100 is installed. The first palatal plate also includes first and second elongate aligning arms 1112 and 1118, respectively, extending from a forward portion of the palatal plate 1110. The first aligning arm 1112 is configured such that when the distractor 1100 is installed, the first aligning arm is positioned adjacent to the labial portion of one or more anterior teeth. The second aligning arm 1118 is configured such that when the distractor 1100 is installed, the second aligning arm is positioned adjacent to the lingual portion of one or more anterior teeth.

Referring to FIG. 12, with the distractor 1100 installed, the posterior teeth disposed between the sides of the palatal plates 1110 and 1150 and the posts 1114, 1116, 1154, and 1156 extending therefrom. The anterior teeth are positioned between the first aligning arms 1112 and 1152 and the second aligning arms 1118 and 1158. The position of the palatal plates 1110 and 1150 relative to each other is selectively adjustable using the screw assembly 60 a portion of which is embedded in or attached to each palatal plate. In this manner, the distractor 1100 can be expanded or contracted, both symmetrically or asymmetrically with respect to the front and back portions. As the distractor 1100 is expanded and contracted, the position of the teeth relative to the distractor is maintained by the posts and retainers. Further, in contrast to previous embodiments, the distractor 1100 is easily removed and installed by the patient.

The following is a protocol of alternate rapid maxillary expansions and slow constrictions (Alt-RMESC). The Alt-RMESC protocol is either effective in patients with or without cleft lip and palate. The Alt-RMESC protocol was developed in 2003 for the growth modification and treatment of constricted or retrusive maxilla in class I, class II, or class III type skeletal discrepancies, not only for the growing patients with cleft lip and palate, but also for those without cleft and also for non-growing patients. The clinical devices and protocol are exactly the same for both groups of patients. The devices are the different embodiments of a dual expanding palatal distractor.

The complete Alt-RMESC protocol involves 8-10 months. The expanded space between the central incisors could be saved for relieving anterior crowding or for compensating dental effects, such as the proclined maxillary incisors due to the protraction.

The HYRAX and HAAS type, fan shape expanders or even double-hinged expanders cannot be as effective as this invention for the opening of circumaxillary sutures under the Alt-RMESC protocol. The key is not only the design of the differential nonparallel expansion capability of the dual screw appliances described here, but also the Alt-RMESC protocol rather than the types of expander.

Several types of rapid maxillary expander have been used for the purpose of maxillary expansion. They are the HYRAX and HAAS type, fan shape expanders or even double-hinged expanders with two acrylic resin halves, splints, or in a hygienic design. These appliances expand and rotate the maxilla outward in a parallel or V-shaped manner.

In case of fan shape expanders or even double-hinged expanders, the center of rotation is located around the posterior nasal spine. The expansion force is distributed not only in the maxilla, but also extends into the circumaxillary structures. It is postulated that this entails bone resorption behind the maxilla and consequently results in posterior displacement of maxilla. On the contrast, it is postulated as well that this entails the circumaxillary structures such as pterygpoid plates to displace the maxilla forward. These two assumptions explain why some of the clinical studies on Hyrax-typed expanders reported an anterior displacement of maxilla, while some others reported no significant displacement or even a posterior displacement of maxilla. The posterior displacement of maxilla compromises the maxillary protraction in Class III patients.

Embodiments of the dual rapid maxillary expander described herein are developed for incremental, differential, nonparallel expansion and constriction of anterior and posterior maxilla. In some embodiments, its configuration has two identical rotation hinges. It includes a jackscrew in the center in front and the back. It expands and rotates each half of the maxilla outward and inward, sequentially in nonparallel increments through the two independent hinges of rotation, one in front and the other in the back. This model of expansion entails forward or backward rotation of maxilla with a lower chance of bone resorption behind the maxillary tuberosities, and this has been verified in an experimental study in cats, that the double-hinged expander significantly displaced the maxilla more anteriorly than the Hyrax expander. Therefore, in terms of the anterior displacement of maxilla, a dual-maxillary expander is superior to the other types of expander for the treatment of a hypoplastic or transversely deficient maxilla in growing or non-growing patients.

The inter-maxillary suture is an osteogenic and osteolytic tissue that allowed for a certain degree of expansion and constriction. Within the biological and physiological limitations, expansion of a suture leads to bone formation, and constriction leads to bone resorption. This phenomenon also has been referred as the sutural distraction osteogenesis and osteolysis, respectively, that resembles the callus distraction osteogenesis or osteolysis in the long bone. For the callus distraction osteogenesis in long bone, it has been revealed that the optimal (biological and physiological) rate of distraction is 1 mm/day, so in this protocol it is recommended between 0.5 to maximum 1 mm of rapid expansion in front every day and in the posterior every other day for 1 first week and between 0.5 to maximum 1 mm of rapid expansion in back every day and in the front every other day for second week, then stop It also has been considered that 1 mm/day is the biological, physiological, and optimal rate for rapid maxillary suture expansion. The optimal rate of expansion or distraction for any osteogenetic tissue, such as suture or callus, is 1 mm/day. To encourage the proper biologic bone formation at the expanded sutural parts, it is recommended in the protocol that a rest period of two months for full ossification of the distracted piece and complete conversion of the expanded soft tissue to boney tissues. The following constriction of the maxillary posterior teeth is at the rate of one turn twice per week, equaling to 0.5 mm constriction of the posterior teeth per week until the upper posterior teeth get close to the lower posterior teeth. This protocol will reduce the chance of bone resorption as result of osteolysis at the sutural tissue, which can impact negatively the transverse dimension of the nasal cavity. The daily expansion of a suture should be biologically and physiologically confined within less than 1 mm/day or constriction of less than 0.5 mm per week. At the completion of the constriction, sequentially the maxilla can have two or three Alt-RMESC until the proper nasal cavity expansion is acquired. In each rapid phase of expansion, the nasal cavity and related bones including; maxillary, palatine, zygomatic bones will expand equal or close to equal of the total maxillary expansion. The slow constriction eliminates the constriction of the nasal cavity. This incremental expansion will eventually provide ideal expansion of the nasal cavity and facial width in maxillary and inter-zygomatic area more efficiently than any existing protocols.

Figure 14:
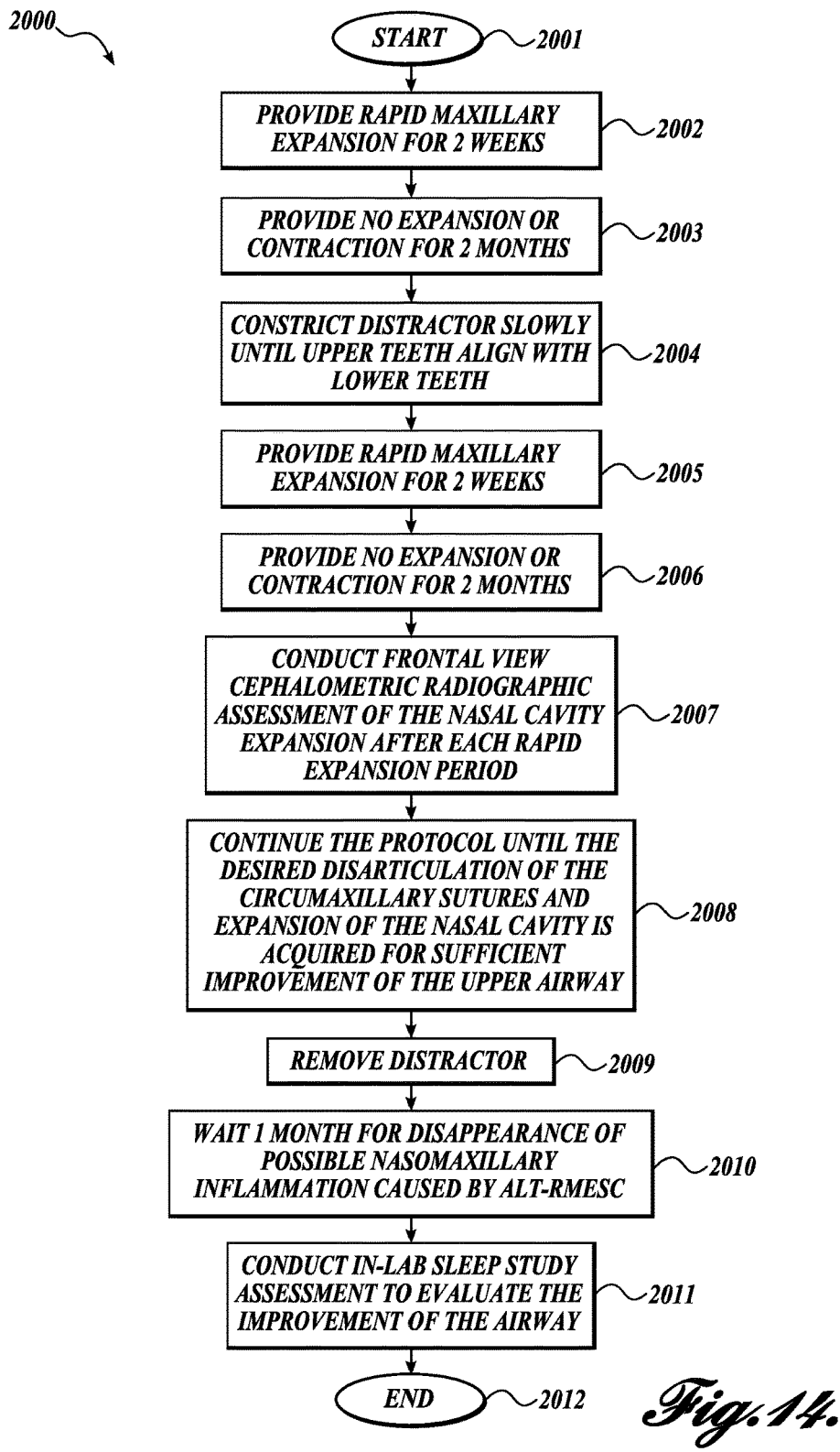
FIG. 14 shows a method of treating a patient using a palatal distractor.

FIG. 14 shows an exemplary method of applying an Alt-RMESC protocol with a total treatment period of 8-10 months, including 3-4 repetitions in sequence. The process starts at step 2001 and proceeds to step 2002, wherein rapid maxillary expansion is provided for approximately 2 weeks. During the first week, rapid maxillary expansion is achieved by turning the front screw turns 2-3 times daily to provide a maximum extension of 1 mm every day. In addition, during this first week, the back screw is turned 2-3 times every other day to loosen the maxillary suture like unzipping the suture, starting in front then continuing toward the back. During the second week, rapid maxillary expansion is achieved by turning the back screw 2-3 times daily to provide a maximum extension of 1 mm every day. During this second week, the front screw is turned 2-3 times every other day to make the expansion equal in back and front if needed.

The process proceeds to step 2003, during which no expansion is provided for approximately 2 months to allow the effective ossification of the expanded soft tissue.

Next, in step 2004, at least two months of slow constriction are achieved by one turn, twice per week, up to a maximum of 0.5 mm dental constriction per week. Constriction is provided until the upper posterior teeth come close to the lower posterior teeth.

In step 2005 rapid maxillary expansion is again provided for approximately 2 weeks. During the first week, rapid maxillary expansion is achieved by turning the front screw turns 2-3 times daily to provide a maximum extension of 1 mm every day. In addition, during this first week, the back screw is turned 2-3 times every other day to loosen the maxillary suture like unzipping the suture, starting in front then continuing toward the back. During the second week, rapid maxillary expansion is achieved by turning the back screw 2-3 times daily to provide a maximum extension of 1 mm every day. During this second week, the front screw is turned 2-3 times every other day to make the expansion equal in back and front if needed.

Next, in step 2006, no expansion or constriction is provided for at least 2 months in order to allow the effective ossification of the expanded soft tissue.

In step 2007, a frontal view cephalometric radiographic assessment of the nasal cavity expansion after each rapid expansion period is performed.

In step 2008, the protocol is continued until the desired disarticulation of the circumaxillary sutures and expansion of the nasal cavity is acquired for sufficient improvement of the upper airway.

Next, in steps 2009 and 2010, the distractor is removed and 1 month is allowed to pass to enable the disappearance of possible nasomaxillary inflammation caused by Alt-RMESC.

Finally, in step 2011, an in-lab sleep study assessment is conducted to evaluate the improvement of the airway.

In an alternative protocol, especially in adult patients, the treatment starts by installation of the upper bonded dual expander device as FIG. 9, then patient will have surgical osteotomy in midpalatal area or as Lefort 1. In one embodiment, the apparatus is activated for expansion beginning 3 to 7 days after osteotomy, depending on the age of patient, at a rate of two to four times daily, every 6 to 12 hours, at a rate of 0.5 to 1 mm per day. This expansion can be in parallel or non-parallel way depending on the requirement of the shape of the opposing dental arch form. In certain cases which require counterclockwise rotation of the maxillary structures, by use of vertical elastics anchored to the lower teeth or temporary implants inserted in the body of mandible, the distraction can be directed vertically in combination of transversely. The transvers and/or vertical expansion of the apparatus is continued until the desired over-expansion is accomplished, then stabilized for 30-60 days after distraction.

In another alternative protocol, the stem cells of the patient can be collected from the blood or bone marrow or in combination with platelet rich plasma injected in the area of distracted bone and surgical site to enhance or facilitate the amount of expansion and shorten the period of stabilization. Periodic panoramic or cone beam computed tomography taken at monthly intervals indicates that the distraction gaps are bridged by new bony regenerate.

This stage of protocol provides significant expansion in the body of the maxilla at the base of the tongue for proper airway expansion. It also widens the maxillary area to overcome narrow maxillary dentoalveolar structures. The over-expansion at the alveolar area enables the next stage of protocol for improvement of recessed gingival areas. The apparatus is activated by slow reverse contraction of 2 turns weekly to constrict the posterior teeth to the final desired width, and embed the teeth back to the newly-formed alveolar bone. In the next stage, a non-extraction orthodontic alignment of the maxillary teeth can be accomplished. This technique and apparatus provide an efficient technique to avoid extraction of the teeth for relieving crowding and can develop an adequate recipient site for insertion of implants to replace the missing teeth and as simple surgical alternatives, can be an excellent adjunct for treatment of obstructive sleep apnea. It can be utilized for correction of midface deformities caused by maxillary transverse, vertical and sagittal deficiencies.

While various embodiments have been illustrated and described, it will be appreciated that various changes can be made therein without departing from the spirit and scope of the claimed subject matter.

The embodiments of the invention in which an exclusive property or privilege is claimed are defined as follows:

1. An orthodontic distractor capable of expansion or constriction to adjust the position of one or more of a patient's upper teeth, jaws, oral cavity and airway, the distractor comprising:
 an adjustable assembly, comprising:
 a first rod and a second rod, each of the first and second rods having a first end and a second end, wherein each of the first and second rods is couplable to upper teeth of a patient;
 a mechanism joining the first and second rods and permitting the first ends of the first and second rods to be pushed apart or pulled together independent of the second ends and which permits the second ends of the first and second rods to be pushed apart or pulled together independent of the first ends;
 a first coupling assembly configured to couple the first rod to a bicuspid and a molar tooth of a patient;
 a second coupling assembly configured to couple the second rod to a bicuspid and a molar tooth of a patient; and
 wherein the first coupling assembly includes first extension arms attached to the first rod, the first extension arms jointly supporting a first elliptical band adapted to extend along occlusal surfaces of a first set of palatal teeth, that includes a bicuspid and a molar, and the second coupling assembly comprises second extension arms coupled to the second rod, the second extension arms jointly supporting a second elliptical band adapted to extend along occlusal surfaces of a second set of palatal teeth, that includes a bicuspid and a molar.

2. A method of treating a patient using a palatal distractor, wherein the palatal distractor comprises at least two independent axes of rotation and is capable of nonparallel distraction, the method comprising:
 expanding a maxillary suture of the patient using the palatal distractor to loosen the maxillary suture of the patient, wherein the expanding comprises expanding a front of the palatal distractor faster than the back area for a first period of time followed by expanding a back of the palatal distractor faster than the front area for a second period of time;
 preventing expansion of the maxillary suture of the patient by maintaining the palatal distractor for a third period of time during which ossification of the expanded maxillary suture occurs; and
 slowly constricting upper teeth of the patient to a particular location after preventing expansion of the maxillary suture of the patient for the third period.

3. The method of claim 2, further comprising:
 assessing a nasal cavity, oral cavity and pharyngeal airway expansion of the patient after expansion of the palate, upper jaw, and upper teeth of the patient and, if the nasal cavity expansion has not reached a particular disarticulation, repeating expanding the maxillary suture of the patient, followed by another slow constriction of the teeth, preventing constriction of the maxillary suture and nasal cavity of the patient.

4. The method of claim 2, wherein each of the first period of time and the second period of time is in a range of 7 to 14 days.

5. The method of claim 2, wherein the second period of time is about 1 to 3 months.

6. The method of claim 2, wherein the particular location of the upper teeth after constriction is a location of the upper teeth with respect to lower teeth of the patient.

7. The method of claim 2, further comprising:
 collecting the stem cells of the patient from at least one of blood bone marrow; and
 injecting the stem cells in the area of distracted bone and surgical site to enhance or facilitate the amount of expansion and shorten the period of ossification.

8. The method of claim 2, further comprising combining the stem cells with platelet-rich plasma prior to injecting the stem cells into the patient.

9. An orthodontic distractor capable of expansion or constriction to adjust the position of one or more of a patient's upper teeth, jaws, oral cavity and airway, the distractor comprising:
 an adjustable assembly, comprising:
 a first rod and a second rod, each of the first and second rods having a first end and a second end, wherein each of the first and second rods is couplable to upper teeth of a patient;
 a mechanism joining the first and second rods and permitting the first ends of the first and second rods to be pushed apart or pulled together independent of the second ends and which permits the second ends of the first and second rods to be pushed apart or pulled together independent of the first ends;
 a first coupling assembly configured to couple the first rod to a bicuspid and a molar tooth of a patient;
 a second coupling assembly configured to couple the second rod to a bicuspid and a molar tooth of a patient;
 the first and second rods each defining an expandable cavity;
 the first coupling assembly includes first and second arm pieces, each the arm piece having an outwardly extending arm section and an engagement section;
 wherein the engagement section of the first arm piece defines a longitudinal cavity that is non-round in transverse dimension and the engagement section of the second arm piece is shaped to matingly fit into the longitudinal cavity of the first arm piece, and wherein the non-round transverse shape of the cavity and the engagement section of the second arm piece prevent relative rotation; and
 wherein the engagement sections join together in the expandable cavity, which is reduced in size to grip the engagement section of the first arm piece, to retain the arm sections in position and orientation.

10. The orthodontic distractor of claim 9, wherein the expandable cavity can be tightened and alternately expanded by fasteners that pass through the cavity and are tightened to tighten the expandable cavity.

11. The orthodontic distractor of claim 9, wherein the longitudinal cavity is polygonal in transverse dimension.

12. The orthodontic distractor of claim 11, wherein the longitudinal cavity is star-shaped in transverse dimension.

* * * * *